(12) United States Patent
Farmer et al.

(10) Patent No.: US 8,821,854 B2
(45) Date of Patent: *Sep. 2, 2014

(54) METHODS FOR INHIBITING MICROBIAL INFECTIONS ASSOCIATED WITH SANITARY PRODUCTS AND FOR ENHANCING SANITARY PRODUCT DEGRADATION

(75) Inventors: Sean Farmer, La Jolla, CA (US); Andrew R. Lefkowitz, La Jolla, CA (US)

(73) Assignee: Ganeden Biotech, Inc., Mayfield Heights, OH (US)

( * ) Notice: Subject to any disclaimer, the term of this patent is extended or adjusted under 35 U.S.C. 154(b) by 1604 days.

This patent is subject to a terminal disclaimer.

(21) Appl. No.: 11/401,701

(22) Filed: Apr. 10, 2006

(65) Prior Publication Data

US 2006/0177429 A1  Aug. 10, 2006

Related U.S. Application Data

(63) Continuation of application No. 10/819,060, filed on Apr. 5, 2004, now Pat. No. 7,025,974, which is a continuation of application No. 09/291,789, filed on Apr. 14, 1999, now Pat. No. 6,716,435, which is a continuation-in-part of application No. PCT/US98/07307, filed on Apr. 10, 1998.

(60) Provisional application No. 60/044,643, filed on Apr. 18, 1997.

(51) Int. Cl.
*A01N 25/34* (2006.01)
*A01N 63/00* (2006.01)
*C12N 1/20* (2006.01)

(52) U.S. Cl.
USPC ............ 424/93.46; 424/402; 435/252.5; 435/832

(58) Field of Classification Search
None
See application file for complete search history.

(56) References Cited

U.S. PATENT DOCUMENTS

| | | | |
|---|---|---|---|
| 3,860,490 A | 1/1975 | Guttag | 195/108 |
| 4,062,943 A | 12/1977 | Lindberg | 424/115 |
| 4,110,477 A | 8/1978 | Naruse et al. | 426/46 |
| 4,210,672 A | 7/1980 | Hata | 426/43 |
| 4,323,651 A | 4/1982 | Long et al. | 435/207 |
| 4,790,989 A | 12/1988 | Hunter et al. | 424/404 |
| 4,871,539 A | 10/1989 | Hata et al. | 424/93 |
| 4,883,478 A | 11/1989 | Lerailler et al. | 604/360 |
| 4,980,180 A | 12/1990 | Cully et al. | 426/47 |
| 5,000,939 A | 3/1991 | Dring et al. | 424/48 |
| 5,002,881 A | 3/1991 | Van Nispen et al. | 435/139 |
| 5,045,314 A | 9/1991 | Bone et al. | 424/93 |
| 5,079,164 A | 1/1992 | Kirkovits et al. | 435/252.5 |
| 5,102,800 A | 4/1992 | Hirikoshi | 435/193 |
| 5,176,911 A | 1/1993 | Tosi et al. | 424/93 |
| 5,190,533 A | 3/1993 | Blackburn | 604/367 |
| 5,200,336 A | 4/1993 | Kong et al. | 435/199 |
| 5,344,647 A | 9/1994 | Rossall | 424/93.462 |
| 5,431,924 A | 7/1995 | Ghosh et al. | 424/522 |
| 5,439,678 A | 8/1995 | Dobrogosz et al. | 424/93.45 |
| 5,455,028 A | 10/1995 | O'Donnell | 424/93.46 |
| 5,464,766 A | 11/1995 | Bruno | 435/187 |
| 5,472,713 A | 12/1995 | Fein et al. | 424/522 |
| 5,540,920 A | 7/1996 | Vinopal et al. | 424/405 |
| 5,602,183 A | 2/1997 | Martin et al. | 514/724 |
| 5,609,768 A | 3/1997 | Mueller et al. | 210/691 |
| 5,624,424 A | 4/1997 | Saisaka et al. | 604/385.2 |
| 5,698,227 A | 12/1997 | Rivlin | 424/522 |
| 5,801,025 A * | 9/1998 | Ohara et al. | 435/139 |
| 5,849,289 A | 12/1998 | Dobrogosz et al. | 424/93.45 |
| 5,938,648 A | 8/1999 | LaVon et al. | 604/358 |
| 6,051,552 A * | 4/2000 | Reid et al. | 514/8 |
| 6,103,246 A | 8/2000 | Tisdale et al. | 424/401 |
| 6,261,577 B1 | 7/2001 | Kessler | 424/401 |
| 6,312,703 B1 | 11/2001 | Orthoefer | 424/401 |
| 6,359,191 B1 | 3/2002 | Rusch et al. | |
| 6,416,772 B1 | 7/2002 | Van Engelen et al. | 424/401 |
| 6,461,607 B1 | 10/2002 | Farmer | 424/93.45 |
| 6,531,126 B2 | 3/2003 | Farmer | 424/115 |

(Continued)

FOREIGN PATENT DOCUMENTS

AU  WO 9208470  5/1992
DE  197 13 908  10/1998

(Continued)

OTHER PUBLICATIONS

Baker et al., "Growth requirements of 94 strains of thermophilic bacilli", *Can. J. Microbiol.*, 6:557-563 (1960).
Bergey's Manual of Systemic Bacteriology, 2:1117 (1986).
Czaczyk et al., "Antifungal activity of *Bacillus coagulans* against *Fusarium* sp. ", *Acta Microbiologica Polonica*, 51(3):275-283 (2002).
Database Medline, Moldenhauer, et al., Abstract only, Database accession No. NLM7489197, Sep. 1995.

(Continued)

*Primary Examiner* — Debbie K Ware
(74) *Attorney, Agent, or Firm* — Mintz Levin Cohn Ferris Glovsky and Popeo, P.C.; Ingrid A. Beattie

(57) ABSTRACT

The present invention describes compositions and methods for inhibiting microbial infections associated with the use of sanitary products, such as diapers, bandages, sanitary napkins, tampons, and the like. The present invention comprises providing for use a sanitary product containing an effective amount of a viable, non-pathogenic, lactic acid-producing bacteria, such as *Bacillus coagulans*, or an extracellular product thereof, useful for inhibiting growth of parasites and pathogens on the epithelial tissue in contact with the sanitary product during use of the product. The present invention also provides for enhancing biodegradation of sanitary products after use and disposal. Also described herein are methods using the product and systems containing the compositions.

22 Claims, No Drawings

(56) References Cited

U.S. PATENT DOCUMENTS

| | | | |
|---|---|---|---|
| 6,579,543 B1 | 6/2003 | McClung | 424/728 |
| 6,645,506 B1 | 11/2003 | Farmer | 424/260.1 |
| 6,716,435 B1 | 4/2004 | Farmer et al. | 424/400 |
| 6,723,326 B1 | 4/2004 | Farmer | 424/246.1 |
| 6,905,692 B2 | 6/2005 | Farmer | 424/260.1 |
| 7,025,974 B2 | 4/2006 | Farmer et al. | 424/400 |
| 7,048,950 B2 | 5/2006 | Farmer | 424/522 |
| 7,232,571 B2 | 6/2007 | Farmer et al. | 424/247.1 |
| 7,371,407 B2 | 5/2008 | Farmer | 424/522 |
| 7,374,753 B1 | 5/2008 | Farmer et al. | 424/93.46 |
| 7,507,402 B1 | 3/2009 | Farmer et al. | 424/94.46 |
| 2001/0033838 A1 | 10/2001 | Farmer | 424/115 |
| 2003/0003107 A1 | 1/2003 | Farmer | 424/184.1 |
| 2003/0031659 A1 | 2/2003 | Farmer | 424/93.45 |
| 2003/0124104 A1 | 7/2003 | Farmer | 424/93.46 |
| 2003/0143262 A1 | 7/2003 | Brusk et al. | 424/443 |
| 2003/0170334 A1 | 9/2003 | Farmer | 424/780 |
| 2004/0208860 A1 | 10/2004 | Farmer | 424/93.45 |
| 2005/0232909 A1 | 10/2005 | Farmer | 424/93.46 |
| 2005/0271756 A1 | 12/2005 | Brattstrom | 424/764 |
| 2005/0271758 A1 | 12/2005 | Farmer | 424/780 |
| 2006/0147544 A1 | 7/2006 | Farmer | 424/526 |
| 2008/0089963 A1 | 4/2008 | Farmer | 424/780 |
| 2008/0206214 A1 | 8/2008 | Farmer | 424/93.46 |
| 2008/0274153 A1 | 11/2008 | Farmer | 424/404 |

FOREIGN PATENT DOCUMENTS

| | | |
|---|---|---|
| GB | 1 204 017 | 9/1970 |
| GB | 2 303 305 | 2/1997 |
| JP | 63-96107 | 4/1988 |
| JP | 3-192200 | 8/1991 |
| JP | 6-166623 | 6/1994 |
| WO | WO 91 00077 | 1/1991 |
| WO | WO 92 13577 | 8/1992 |
| WO | WO 93/14187 | 7/1993 |
| WO | WO 94/11492 | 5/1994 |
| WO | WO 97/02846 | 1/1997 |
| WO | WO-98/44884 A2 | 10/1998 |
| WO | WO 98 47374 | 10/1998 |
| WO | WO 98/54982 | 12/1998 |
| WO | WO 00/07606 | 2/2000 |
| WO | WO 00/10582 | 3/2000 |
| WO | WO 00/61201 | 10/2000 |

OTHER PUBLICATIONS

Database WPI, Abstract only, Section Ch, Week 199309, Derwent Publications Ltd., London, GB, AN 1993-073946.
Database WPI, Abstract only, Section Ch, Week 199637, Derwent Publications Ltd., London, GB, AN 1996-368043.
Database WPI, Abstract only, Section Ch, Week 199734, Derwent Publications Ltd., London, GB, AN 1997-367033.
Elmer et al., "A neglected modality for the treatment and prevention of selected intestinal and vaginal infections", *JAMA*, 275(11):870-876 (1996).
Evans, E,G.V., "Tinea pedis: clinical experience and efficacy of short treatment", *Dermatology*, 194(suppl. 1):3-6 (1997),.
Evans, E.G.V., "Topical terbinafine (Lamisil®) for superficial mycoses: high cure rates in short treatment times", *J. Dermatol. Treat.*, 9:513-516 (1998).
Fuller, R., "Probiotics in man and animals.\", *J. Appl. Bacteria.*, 66: 365-378 (1989).
Gandhi, a.B., "*Lactobacillus sporogenes*: an advancement in *Lactobacillus* therapy", *Townsend Lett. Doctors & Patients*, pp. 108-110 (1996).
Gibson, et al., "Selective stimulation of Bifidobacteria in the human colon by oligofructose and inulin", *Gastroenterology*, 108: 975-982 (1995).
Gorbach, S.L., "Lactic acid bacteria and human health", *Ann. Med.*, 22(1):37-41 (1990).
Gupta et al., "An overview of topical antifungal therapy in dermatomycoses", *Drugs*, 55(5):645-674 (1998).
Hata, et al., "Meningitis caused by *Bifidobacterium* in an infant", *Pediatr. Infect. Dis.*, 7: 669-671 (1988).
Hill et al., "Vaginitis: current microbiologic and clinical concepts", *Can. Med. Assoc. J.*, 134:321-331 (1986).
Hodges et al., "Potential biocontrol of *Sclerotinia homeocarpa* and *Bipolaris sorokiniana* on the phylloplane of *Poa pratensis* with strains of *Pseudomonas* spp.", *Plant Pathol.*, 43:500-506 (1994).
Klaenhammer, T.R., *FEMS Microbiol. Rev.*, 12(1-3):39-85 (1993).
Lidbeck et al., "*Lactobacilli*, anticarcinogenic activities and human intestinal microflora", *Eur. J. Cancer Prev.*, 1:341-353 (1992).
Malin et al., "Promotion of IgA immune response in patients with Crohn's disease by oral bacteriotherapy with *Lactobacillus* GG", *Ann. Nutr. Metab.*, 40:137-145 (1996).
Marsh, "Antimicrobial strategies in the prevention of dental caries", *Caries Res.*, 27:72-76 (1993).
McNeely et al., "Butenafine", *Drugs*, 55(3):405-412 (1998).
Mitchell, P., "Rearming in the fight against bacteria", *Lancet*, 352:462-463 (1998).
Mohan et al., "Short term hypolipidemic effects of oral *Lactobacillus sporogenes* therapy in patients with primary dyslipidemias", *Indian Heart Journal*, 42(5):361-364 (1990).
Nakamura, et al., "Taxonomic study for *Bacillus coagulans* Hammer", *J. Systematic Bacteriol*, 38:63-73 (1988).
O'Sullivan et al., "Probiotic bacteria: myth or reality?", *Trends in Food Service & Te3chnology*, 31:309-314 (1992).
Perdigon et al., "Symposium: probiotic bacteria for humans: clinical systems for evaluation of effectiveness", *J. Dairy Sci.*, 78:1597-1606 (1995).
Ploysangam et al., "Childhood white superficial anychomycosis caused by *Trichophyton rubrum*: report of seven cases and review of the literature", *J. Am. Acade. Dermatol.*, 36:29-32 (1997).
Rafter, J.J., "The role of lactic acid bacteria in colon cancer prevention", *Scand. J. Gastroenterol.*, 30(6):497-502 (1995).
Reid, et al, "Is there a role for *Lactobacilli* in prevention of urogenital and intestinal infections?" *Clin. Microbiol. Rev.*, 3: 335-344 (1990).
Saavedra, "Feeding of *Bifidobacterium bifidum* and *Streptococcus thermophilus* to infants in hospital for prevention of diarrhoea and shedding of rotavirus", *Lancet*, 344:1046-1049 (1994).
Salminen et al., "Clinical uses of probiotics for stabilizing the gut mucosal barrier: successful strains and future challenges", *Antonie Van Leeuwenhoek*, 70:347-358 (1996).
Schoeni, et al., "Inhibition of *Campylobactger jejuni* colonization in chicks by defined competitive exclusion bacteria", *Applied Environ. Microbiol.*, 60(4):1191-1197 (1994).
Seligman, S.A., "Doderlein's *Bacillus*: friend or foe?", *Br. J. Obstetrics Gynaecol.*, 02:763-764 (1995).
Shannon, "Multiple-antibiotic-resistant *Salmonella*", *Lancet*, 352: 490-491 (1998).
Siegel et al., "Clearance of *Bacillus sphaericus* and *Bacillus thuringiensis*sp. Israelensis from mammals", *J. Econ. Entomol.*, 83(2):347-355 (1990).
Snowden et al., "Anti-inflammatory activity of EMU oils in rats", *Inflammopharmacology*, 5:127-132 (1997).
Sussman, et al., "Clinical manifestations and therapy of *Lactobacillus endocarditis*: report of a case and review of the literature", *Rev. Infect. Dis.*, 8:771-776 (1986).
Sytnik, S.I., "Antagonistic action of corinebacteria and bacilli of cutaneous ecotype on staphylococci", *Mikrobiologicheskii Zhumal*, (in Russian) English Abstract only, 51(1):82-87 (1989).
Thomason, et al, "Bacterial vaginosis: current review with indications for asymptomatic therapy", *Am. J. Obstet. Gynecol.*, 165:1210-1217 (1991).
Williamson, J., "Prescribing problems in the elderly", *The Practitioner*, 220:740-755 (1978).
Winberg, et al., "Pathogenesis of urinary tract infection-experimental studies of vaginal resistance to colonization", *Pediatr. Nephrol.*, 7:509-514 (1993).
Zemtsov et al., "Moisturizing and cosmetic properties of emu oil: A pilot double blind study", *Australasian J. Dermatol.*, 37:159-162 (1996).

\* cited by examiner

METHODS FOR INHIBITING MICROBIAL INFECTIONS ASSOCIATED WITH SANITARY PRODUCTS AND FOR ENHANCING SANITARY PRODUCT DEGRADATION

CROSS REFERENCE TO RELATED APPLICATIONS

This application is a continuation application of U.S. Ser. No. 10/819,060 filed Apr. 5, 2004, now U.S. Pat. No. 7,025,974, which is a continuation application of U.S. Ser. No. 09/291,789 filed Apr. 14, 1999, now U.S. Pat. No. 6,716,435, which is a continuation-in-part of application Serial No. PCT/US98/07307, filed Apr. 10, 1998, which claims priority to application Ser. No. 60/044,643, filed Apr. 18, 1997, (now abandoned), the disclosures of which are hereby incorporated by reference in their entireties.

TECHNICAL FIELD

The claimed invention relates to systems and methods to inhibit microbial infections and to promote epithelial probiosis when using sanitary health care products such as disposable diapers and other sanitary products. In particular, the claimed invention describes use of probiotic lactic acid bacteria in combination with sanitary health care products to inhibit microbial infections, promote dermal probiosis, and enhance biodegradatability of disposed sanitary products.

BACKGROUND OF THE INVENTION

Sanitary products are widely used in various formats for personal hygiene and medical necessity, and include sanitary napkins, diapers, incontinence guards, wound dressings and the like. By their use, a local tissue environment is produced which promotes growth of microbial pathogens, local infections, irritation, rashes, and related problems.

In addition, disposal of used sanitary products is a major environmental and health care concern. The volume of material and the type of material present in the used sanitary product, due to its absorbent character and purpose of collecting body fluids and waste materials, provides a biological and environmental hazard in disposal of used sanitary products. There is a great need for improvements in biodegradation of used sanitary products—degradation of both the product itself and the waste product it contains.

The claimed invention uses a bacterium that is probiotic and heterotrophic to resolve both of the above problems (i.e., to inhibit microbial infections associated with use of sanitary products, and to promote biodegradation of the sanitary product after use).

Probiotic microorganisms are those which confer a benefit when grow in a particular environment, often by inhibiting the growth of other biological organisms in the same environment. Examples of probiotic organisms include bacteria and bacteriophages which possess the ability to grow within the gastrointestinal tract, at least temporarily, to displace or destroy pathogenic organisms, as well as providing other benefits to the host. See e.g., Salminen et al, 1996. *Antonie Van Leeuwenhoek* 70: 347-358; Elmer et al, 1996. *JAMA* 275: 870-876; Rafter, 1995. *Scand. J. Gastroenterol.* 30: 497-502; Perdigon et al, 1995. *J. Dairy Sci.* 78: 1597-1606; Gandi, Townsend Lett. Doctors & Patients, pp. 108-110, Jan. 1994; Lidbeck et al, 1992. *Eur. J Cancer Prev.* 1: 341-353.

The majority of previous studies on probiosis have been observational rather than mechanistic in nature, and thus the processes responsible for many probiotic phenomena have yet to be quantitatively elucidated. Some probiotics are members of the normal colonic microflora and are not viewed as being overtly pathogenic. However, these organisms have occasionally caused infections (e.g., bacteremia) in individuals who are, for example, immunocompromised. See e.g., Sussman, J. et al., 1986. *Rev Infect. Dis.* 8: 771-776; Hata, D. et al., 1988. *Pediatr. Infect. Dis.* 7: 669-671.

For example, the probiotic bacteria found in sour milk, has been utilized since ancient times (i.e., long-before the discovery of bacteria) as a therapeutic treatment for dysentery and related gastrointestinal diseases. More recently, probiotic preparations were systematically evaluated for their effect on health and longevity in the early-1900's (see e.g., Metchinikoff, E., *Prolongation of Life*, Willaim Heinermann, London 1910), although their utilization has been markedly limited since the advent of antibiotics in the 1950's to treat pathological microbes. See e.g., Winberg, et al, 1993. *Pediatr. Nephrol.* 7: 509-514; Malin et al, *Ann. Nutr. Metab.* 40: 137-145; and U.S. Pat. No. 5,176,911. Similarly, lactic acid-producing bacteria (e.g., *Bacillus*, *Lactobacillus* and *Streptococcus* species) have been utilized as food additives and there have been some claims that they provide nutritional and/or therapeutic value. See e.g., Gorbach, 1990. *Ann. Med.* 22: 37-41; Reid et al, 1990. *Clin. Microbiol. Rev.* 3: 335-344.

The nutritional use of probiotic bacteria, especially *Lactobacillus* and *Biffidobacterium* strains, that colonize the gut has been previously disclosed (Winberg, et al., *Pediatr. Nephrol.* 7: 509-514, 1993; Malin, et al., *Ann. Nutr. Metab.* 40:137-145, 1996; and U.S. Pat. No. 4,176,911). Lactic acid producing bacteria (e.g., *Bacillus, Lactobacillus* and *Streptococcus* species) have been used as food additives and there have been some claims that they provide nutritional and therapeutic value (Gorbach, *Ann. Med.* 22: 37-41, 1990; Reid, et al., *Clin. Microbiol. Rev.*, 3: 335-344, 1990). Heterotrophic bacteria play an important role in the biodegradation of animal waste and many natural and synthetic polymers. Bacterial strains including: *Bacillus, Pseudomonas, Arthrobacter, Achromobacter, Micrococcus* and *Rhodococcus* have been shown to participate in the breakdown of waste products, cellulose materials, petroleum hydrocarbons and their associated products, such as plastics, synthetic rubbers and other synthetic materials.

*Bacillus coagulans* is a non-pathogenic gram positive spore-forming bacteria that produces L(+) lactic acid (dextrorotatory) in homofermentation conditions. It has been isolated from natural sources, such as heat-treated soil samples inoculated into nutrient medium (Bergey's Manual off Systemic Bacteriology, Vol. 2, Sneath, P. H. A., et al., eds., Williams & Wilkins, Baltimore, Md., 1986). Purified *B. coagulans* strains have served as a source of enzymes including endonucleases (e.g., U.S. Pat. No. 5,200,336); amylase (U.S. Pat. No. 4,980,180); lactase (U.S. Pat. No. 4,323,651); and cyclo-malto-dextrin glucano-transferase (U.S. Pat. No. 5,102,800). *B. coagulans* has been used to produce lactic acid (U.S. Pat. No. 5,079,164). A strain of *B. coagulans* (referred to as *L. sporogenes*; Sakaguti & Nakayama (ATCC 31284)) has been combined with other lactic acid producing bacteria and *B. natto* to produce a fermented food product from steamed soybeans (U.S. Pat. No. 4,110,477).

Use of a sanitary product produces frequent dermal mucoidal irritations and/or infections associated with the use of the product. Diaper rash is a common issue in both adults and infants. Rashes can become more serious irritations when opportunistic pathogens introduced into the sanitary product germinate and cause infections on these irritated sites. In addition, vulva-vaginal infections are common with the use of napkins and tampons and are typically caused by *Candida* or *Gardnerella* species (e.g., *Candida albicans* and *C. tropicalis*). Toxic Shock Syndrome and other dermal infections caused by *Staphylococcal* bacteria (e.g., *Staphylococcus aureus* and *S. epidermidis* are also common). Other pathogens which can cause infection after brief periods of dermal irritation and/or use of sanitary products include Trichophyton species (e.g., *T. mentagrophytes*).

In addition, disposable diapers and other sanitary products present environmental problems in their disposal. Sanitary landfills are overused and accumulate excessive amounts of disposed products. Sanitary products such as diapers, sanitary napkins and tampons biodegrade slowly and occupy considerable space due to the bulk of these products, particularly when containing body excrements or fluids which expand due to their absorbent polymer content.

SUMMARY OF THE INVENTION

It has now been discovered that probiotic acid-producing bacteria are effective in inhibiting, preventing and/or eliminating dermal/epithelial infections by preventing the growth of dermal pathogens which grow upon use of diapers and other sanitary products.

It has also been discovered that bacterial enzymes and other metabolic products of probiotic acid-producing bacteria play an important role in the biodegradation of many sanitary products, including biodegradation of the waste biomaterials, such as when disposed in landfills.

The claimed invention discloses compositions and articles of manufacture containing non-pathogenic probiotic acid-producing bacteria, and their methods of use for inhibiting pathogen growth on skin in applications where sanitary products are used, which also provides for degradation of the sanitary products and body waste products contained thereby. The invention contemplates sanitary products as articles of manufacture which contain effective amounts of a probiotic bacterium in various parts of the product so as to achieve the desired result of inhibiting microbial infections on the tissues in contact with the sanitary product and/or enhance biodegradation of the sanitary product and waste products collected upon the sanitary product.

Typically, the probiotic acid-producing bacteria is introduced into or onto portions of the sanitary product by applying a composition containing viable bacteria to the product during a stage of the manufacture of the sanitary product.

In preferred embodiments, the invention contemplates using a lactic acid-producing bacteria, and more preferably using spore-forming Bacillus species, particularly *B. coagulans*, being a preferred embodiment, and *B. coagulans Hammer* being a particularly preferred embodiment.

In one embodiment of the composition, a *Bacillus coagulans* strain is included in the composition in the form of spores. In another embodiment, a *Bacillus coagulans* strain is included in the composition in the form of a dried cell mass. In another embodiment, a *Bacillus coagulans* strain is included in the composition in the form of a stabilized paste. In another embodiment, a *Bacillus coagulans* strain is included in the composition in the form of stabilized gel.

In one embodiment, the composition further includes an effective amount of a bifidogenic oligosaccharide, such as a short or long chain fructooligosaccharide (FOS), a gluco-oligosaccharide or other long-chain oligosaccharide polymer not readily digested by pathogenic bacteria as described herein.

It should be understood that both the foregoing general description and the following detailed description are exemplary and explanatory only and are not restrictive of the invention as claimed.

DETAILED DESCRIPTION OF THE INVENTION

The present invention is directed to the discovery that non-pathogenic lactic acid-producing bacteria (i.e., "lactic acid bacteria"), such as the exemplary *Bacillus coagulans*, can be used in compositions as a probiotic for inhibiting growth of microbial dermal and epithelial pathogens which can occur upon use of various sanitary products. Typically, these bacteria can be used as a preventative or ameliorative treatment of rashes and other dermal infections that manifest themselves as a result of use of the sanitary product, including irritated/inflamed skin, dermatitis, excema, or skin allergies.

In addition, the invention describes the use of one or more bacteria species to enhance degradation of the sanitary product, which are included in the compositions, methods and articles of manufacture of this invention and are referred to herein as "degradative bacteria".

A sanitary product can be any of variety of materials used in contact with a body tissue which, upon use, is susceptible to dermal or epithelial rashes and/or infections. Exemplary sanitary products include an infant or adult diaper, sanitary napkin, tampon, incontinence guard, bed sheet or protector, wound or sore dressing, dermal patch, adhesive tape, saliva absorbent, and related disposable sanitary and hygiene products, although the invention need not be viewed as so limited.

The invention therefore describes various compositions, methods for using the compositions and systems containing the compositions. In preferred embodiments, the composition further comprises an effective amount of a bifidogenic oligosaccharide, such as fructo-oligosaccharide (FOS), gluco-oligosaccharide (GOS) and the like, as described herein.

A. Probiotic Acid-Producing Bacteria

A probiotic acid-producing bacteria suitable for use in the methods and compositions of the invention as defined for use in the present invention produces acid and is non-pathogenic. There are many suitable bacteria identified as described herein, although the invention is not limited to currently known bacterial species insofar as the purposes and objectives of the bacteria is described. The property of acid production is key to the effectiveness of the probiotic lactic acid-producing bacteria of this invention because the lactic acid production increases acidity in the local microfloral environment, which does not support growth of many deleterious and undesirable bacteria and fungi. By the mechanism of lactic acid production, the probiotic inhibits growth of competing and deleterious bacteria.

As used herein, "probiotic" refers to microorganisms that form at least a part of the transient or endogenous flora and thereby exhibit a beneficial prophylactic and/or therapeutic effect on the host organism. Probiotics are generally known to be safe by those skilled in the art (i.e., non-pathogenic). Although not wishing to be bound by any particular mechanism, the prophylactic and/or therapeutic effect of an lactic acid-producing bacteria of this invention results in part from competitive inhibition of growth of pathogens due to superior colonization, parasitism of undesirable microorganisms, lactic acid production and/or other extracellular products having antimicrobial activity, or combinations thereof. These products and activities of an lactic acid-producing bacteria of this invention act synergistically to produce the beneficial probiotic effect.

Typical lactic acid-producing bacteria (i.e., a "lactic acid bacteria") useful as a probiotic of this invention are efficient acid producers which include non-pathogenic members of the *Bacillus* genus, all members of the *Lactobacillus* and *Sporolactobacillus* genus, all members of the *Bifidobacterium* genus, and *Pseudomonas limbergii*, although certain species are particularly preferred as described herein.

Preferred lactic acid-producing bacteria include the *Bacillus laterosporus* or *Bacillus subtilis* species described herein, including *Bacillus laterosporus, Bacillus laterosporus* BOD, *Bacillus laterosporus laubach* and *Bacillus subtilis*.

More preferably, the present invention contemplates the use of a lactic acid-producing bacteria ("lactic acid bacteria") which includes the above *Lactobacillus, Biffidobacterium* and certain *Bacillus* species. Particularly preferred are lactic acid-producing bacteria, such as *L. sporogenes* (aka *B. coagulans*), *Sporolactobacillus* P44, and *Bacillus brevis* subsp. *coagulans*.

Exemplary lactic acid-producing, non-pathogenic *Bacillus* species are *Bacillus coagulans, Bacillus coagulans Hammer, Bacillus brevis* subspecies *coagulans* and *Bacillus laevolacticus*.

Exemplary lactic acid-producing *Lactobacillus* species include *Lactobacillus acidophilus, Lactobacillus bulgaricus, Lactobacillus casei, Lactobacillus cereale, Lactobacillus DDS-1, Lactobacillus delbrukeii, Lactobacillus fermentum, Lactobacillus gaserii, Lactobacillus GG, Lactobacillus jensenii, Lactobacillus rhamnosus, Lactobacillus plantarum, Lactobacillus salivarius, Lactobacillus sporogenes* (aka *B. coagulans*) and *Lactobacillus thermophilus*.

Exemplary lactic acid-producing Sporolactobacillus species include all *Sporolactobacillus* species, including *Sporolactobacillus* P44.

Exemplary lactic acid-producing *Bifidobacterium* species include: *Bifidobacterium adolescentis, Bifidobacterium animalis, Bifidobacterium bifidum, Bifidobacterium bifidus, Bifidobacterium breve, Bifidobacterium infantis, Bifidobacterium infantus* and *Bifidobacterium longum*.

There are several *Bacillus* species particularly useful as a probiotic according to the present invention, including the lactic acid-producers *Bacillus coagulans*, and *Bacillus laevolacticus*.

It should be noted that although exemplary of the present invention, *Bacillus coagulans* is only a model for the other lactic acid producing species of probiotic bacteria useful in the practice of the present invention, and therefore the invention is not to be considered as limiting and it is intended that any of the acid producing species of probiotic bacteria can be used in the compositions, therapeutic systems and methods of the present invention.

There are a variety of different *Bacillus* species useful in the present invention, including, but not limited to many different strains available through commercial and public sources, such as the American Type Culture Collection (ATCC). For example, *Bacillus coagulans* strains are available as ATCC Accession Numbers 15949, 8038, 35670, 11369, 23498, 51232, 11014, 31284, 12245, 10545 and 7050. *Bacillus laevolacticus* strains are available as ATCC Accession Numbers 23495, 23493, 23494, 23549 and 23492. A *Bacillus* species is particularly suited for the present invention, particularly species having the ability to form spores which are relatively resistant to heat and other conditions, making them ideal for storage (shelf-life) in product formulations, and ideal for survival and colonization of tissues under conditions of pH, salinity, and the like on tissues of the skin and epithelium. Additional useful properties include being non-pathogenic, aerobic, facultative and heterotrophic, rendering these species safe, and able to colonize skin and epithelium.

Because *Bacillus* spores are heat-resistant and additionally can be stored as a dry power, they are particularly useful for formulation into and manufacture of dry products such as the various sanitary products and compositions described herein. Heat and pressure-resistant spores are also suitable for use in pressure-treated absorbent compositions described herein.

Exemplary methods and compositions are described herein using *Bacillus coagulans* as a probiotic. Purified *Bacillus coagulans* is particularly useful as a probiotic in the present invention. Probiotic *B. coagulans* is non-pathogenic and is generally regarded as safe (i.e., GRAS classification) by the U.S. Federal Drug Administration (FDA) and the U.S. Department of Agriculture (USDA), and by those skilled in the art. The Gram positive rods of *B. coagulans* have a cell diameter of greater than 1.0 micrometer ($\mu m$) with variable swelling of the sporangium, without parasporal crystal production.

Because *B. coagulans* forms heat-resistant spores, it is particularly useful for making pharmaceutical compositions that require heat and pressure in their manufacture. Formulations that include viable *B. coagulans* spores in a pharmaceutically acceptable carrier are particularly preferred for making and using compositions according to the present invention.

The growth of these various *Bacillus* species to form cell cultures, cell pastes and spore preparations is generally well known in the art. Exemplary culture and preparative methods are described herein for *Bacillus coagulans* and can readily be used and/or modified for growth of the other lactic acid producing bacteria of this invention.

1. Sources of *Bacillus coagulans*

Purified *Bacillus coagulans* bacteria utilized in the present invention are available from the American Type Culture Collection (ATCC, Rockville, Md.) using the following accession numbers: *Bacillus coagulans* Hammer NRS 727 (ATCC No. 11014); *Bacillus coagulans* Hammer strain C (ATCC No. 11369); *Bacillus coagulans* Hammer (ATCC No. 31284; available to the public via the ATCC); and *Bacillus coagulans* Hammer NCA 4259 (ATCC No. 15949). Purified *Bacillus coagulans* bacteria are also available from the Deutsche Sarumlung von Mikroorganismen and Zellkuturen GmbH (Braunschweig, Germany) using the following accession numbers: *Bacillus coagulans* Hammer 1915 (DSM No. 2356); *Bacillus coagulans* Hammer 1915 (DSM No. 2383, corresponds to ATCC No. 11014); *Bacillus coagulans* Hammer (DSM No. 2384, corresponds to ATCC No. 11369); and *Bacillus coagulans* Hammer (DSM No. 2385, corresponds to ATCC No. 15949). *Bacillus coagulans* bacteria can also be obtained from commercial suppliers such as Sabinsa Corporation (Piscataway, N.J.) or K.K. Fermentation (Kyoto, Japan).

*Bacillus coagulans* strains and their growth requirements have been described previously (see e.g., Baker, D. et al, 1960. *Can. J. Microbiol.* 6: 557-563; Nakamura, H. et al, 1988. *Int. J. Svst. Bacteriol.* 38: 63-73. In addition, various strains of *Bacillus coagulans* can also be isolated from natural sources (e.g., heat-treated soil samples) using well-known procedures (see e.g., *Bergey's Manual of systemic Bacteriology*, Vol. 2, p. 1117, Sneath, P. H. A. et al., eds., Williams & Wilkins, Baltimore, Md., 1986).

It should be noted that *Bacillus coagulans* had previously been mis-characterized as a *Lactobacillus* in view of the fact that, as originally described, this bacterium was labeled as *Lactobacillus sporogenes* (See Nakamura et al. 1988. *Int. J.*

*Syst. Bacteriol.* 38: 63-73). However, initial classification was incorrect due to the fact that *Bacillus coagulans* produces spores and through metabolism excretes L(+)-lactic acid, both aspects which provide key features to its utility. Instead, these developmental and metabolic aspects required that the bacterium be classified as a lactic acid *bacillus*, and therefore it was re-designated. In addition, it is not generally appreciated that classic *Lactobacillus* species are unsuitable for colonization of the gut due to their instability in the harsh (i.e., acidic) pH environment of the bile, particularly human bile. In contrast, *Bacillus coagulans* is able to survive and colonize the gastrointestinal tract in the bile environment and even grown in this low pH range. In particular, the human bile environment is different from the bile environment of animal models, and heretofore there has not been any accurate descriptions of *Bacillus coagulans* growth in human gastrointestinal tract models.

2. Growth of *Bacillus coagulans*

*Bacillus coagulans* is aerobic and facultative, grown typically in nutrient broth, pH 5.7 to 6.8, containing up to 2% (by wt) NaCl, although neither NaCl nor KCl are required for growth. A pH of about 4 to about 7.5 is optimum for initiation of growth from spores. It is optimally grown at about 30° C. to about 45° C., and the spores can withstand pasteurization. It exhibits facultative and heterotrophic growth by utilizing a nitrate or sulphate source. Additional metabolic characteristics of *B. coagulans* are summarized in Table 1.

TABLE 1

| Characteristic | *Bacillus coagulans* Response |
| --- | --- |
| Catalase production | Yes |
| Acid from D-Glucose | Yes |
| Acid from L-Arabinose | Variable |
| Acid from D-Xylose | Variable |
| Acid from D-Mannitol | Variable |
| Gas from Glucose | Yes |
| Hydrolysis of Casein | Variable |
| Hydrolysis of Gelatin | No |
| Hydrolysis of Starch | Yes |
| Utilization of Citrate | Variable |
| Utilization of Propionate | No |
| Degradation of Tyrosine | No |
| Degradation of Phenylalanine | No |
| Nitrate reduced to Nitrite | Variable |
| Allatoin or Urate Required | No |

*Bacillus coagulans* can be grown in a variety of media, although it has been found that certain growth conditions produce a culture which yields a high level of sporulation. For example, sporulation is enhanced if the culture medium includes 10 milligrams per liter of manganese sulfate, yielding a ratio of spores to vegetative cells of about 80:20. In addition, certain growth conditions produce a bacterial spore which contains a spectrum of metabolic enzymes particularly suited for the present invention (i.e., production of lactic acid and enzymes for the enhanced probiotic activity and biodegradation). Although spores produced by these particular growth conditions are preferred, spores produced by any compatible growth conditions are suitable for producing a *B. coagulans* useful in the present invention.

Suitable media for growth of *B. coagulans* include Nutristart 701, 2DB (potato dextrose broth), TSB (tryptic soy broth) and NB (nutrient broth), all well known and available from a variety of sources. Media supplements containing enzymatic digests of poultry and fish tissue, and containing food yeast are particularly preferred. A preferred supplement produces a media containing at least 60% protein, and about 20% complex carbohydrates and 6% lipids. Media can be obtained from a variety of commercial sources, notably DIFCO (Detroit, Mich.), Oxoid (Newark, N.J.), BEL (Cockeyesville, Md.), Advanced Microbial Systems, (Shakopee, Minn.), and Tray Biologicals (Tray, Mich.) A preferred procedure for preparation of *B. coagulans* is described in the Examples section, infra.

3. Probiotic Antimicrobial Activity of *Bacillus coagulans*

One aspect of the utility of *B. coagulans* in the present invention is based on the ability of probiotic *B. coagulans* to inhibit growth of pathogenic enteric microorganisms as described in the Examples. Pathogenic bacteria inhibited by *B. coagulans* activity include: *Staphylococcus aureus, S. epidermidis, Streptococcus pyogenes, S.* spp., *Pseudomonas aeruginosa, Escherichia coli* (enterohemorragic species), *Clostridium* species including *C. perfingens, C. difficile, C. botulinum, C. tributrycum,* and *C. sporogenes, Gardnerella vaginalis, Propionibacterium acnes, Aeromonas hydrophilia, Candida* species, *Proteus* species, *Klebsiella* species, fungal dermatophytes or other mycotic pathogens. These pathogens can cause a variety of pathologies including disruption of normal tissue function, and the like conditions as are well known in the art. Therefore, use of compositions containing a probiotic that inhibits these pathogens are useful in preventing or treating conditions associated with infection by these pathogens.

Although *B. coagulans* is exemplary, by virtue of the common properties of a lactic acid-producing bacteria, a therapeutic composition comprising an acid bacterium of this invention can be used in a method or composition of this invention.

4. Extracellular Products Having Antimicrobial Activity

*B. coagulans* cultures contain secreted products which have antimicrobial activity. These secreted products are useful in therapeutic compositions according to the present invention. Cell cultures are harvested as described herein, and the culture supernatants are collected, by filtration or centrifugation, or both, and the resulting supernatant contains antimicrobial activity useful in a therapeutic composition. The preparation of a *B. coagulans* extracellular product is described in the Examples section, infra.

Extracellular products of *B. coagulans* may be included in compositions for use in the invention. In particular, an effective amount of an extracellular product can be applied to a structural component part of a sanitary product of this invention, such as a diaper, bandage, sanitary napkin, tampon and the like product.

B. Degradative Bacteria

In one embodiment, the claimed invention contemplates that the bacteria used in a sanitary product, system or related method according to the present invention have the ability to support biodegradation of the product as an additional feature of the invention. To that end the product, system or method comprises a degradative bacteria as described herein.

A degradative bacteria, or "degradation-enhancing" non-pathogenic bacteria, can be any of the bacteria previously recited which are defined as a probiotic, lactic acid-producing bacteria herein which have the property of being a degradative bacteria, or can be a different bacteria, such that two different species of bacteria are used in practicing the claimed invention. That is, is one embodiment both a probiotic acid-producing bacteria and a degradative bacteria are included in a composition, product, system or method according to the present invention.

Typical bacterial are any non-pathogenic bacteria which promotes degradation of human waste products, and preferably also can degrade the absorbent materials of the sanitary product of the present invention. A preferred bacteria is any non-pathogenic member of the *Bacillus* genus, *Lactobacillus* genus, *Sporolactobacillus* genus, *Bifidobacterium* genus, *Pseudomonas* genus, and the like bacteria.

Particularly preferred members of the *Bacillus* genus include: *Bacillus acidocaldarius, Bacillus alcalophilus, Bacillus azotoformans, Bacillus badius, Bacillus brevis, Bacillus brevis* subsp. *coagulans, Bacillus cereus, Bacillus chitinosporus, Bacillus circulans, Bacillus coagulans, Bacillus dextrolacticus, Bacillus firmus, Bacillus globisporus, Bacillus hydrophilus, Bacillus laevolacticus, Bacillus laterosporus* BOD, *Bacillus laterosporus* Laubach, *Bacillus lentus, Bacillus licheniformis, Bacillus macerans, Bacillus marinus, Bacillus megaterium, Bacillus modestus, Bacillus mycoides, Bacillus pantothenticus, Bacillus pumilus, Bacillus polymyxa, Bacillus smithii, Bacillus stereothermophilus, Bacillus subtilis, Bacillus thermoacidurans, Bacillus thuringiensis, Bacillus uniflagellatus*, and the like.

Particularly preferred members of the *Pseudomonas* genus include *Pseudomonas alcaligenes, Pseudomonas limbergii, Pseudomonas pseudoalcaligenes*, and *Pseudomonas* 679-2.

Particularly preferred members of the *Bifidobacterium* genus include *Bifidobacterium adolescentis, Bifidobacterium animalis, Bifidobacterium bifid.um, Bifidobacterium bifidus, Bifidobacterium breve, Bifidobacterium infantis, Bifidobacterium infantus, Bifidobacterium longum*, and the like.

Particularly preferred members of the *Lactobacillus* genus include *Lactobacillus acidophilus, Lactobacillus bulgaricus, Lactobacillus casei, Lactobacillus cereale, Lactobacillus delbrukeii, Lactobacillus* DDS-1, *Lactobacillus fermentum, Lactobacillus gaserii, Lactobacillus* GG, *Lactobacillus jensenii, Lactobacillus plantarum, Lactobacillus rhamnosus, Lactobacillus salivarius, Lactobacillus sporogenes, Lactobacillus thermophilus*, and the like.

A preferred member of the *Sporolactobacillus* genus include *Sporolactobacillus* P44.

Degradation of waste products or sanitary products can be readily assessed by any of a variety of processes, and therefore the term "degradation-enhancing" is not to be construed as so limited to any particular degree or rate of enhancement of degradation.

The above bacteria are well known in the bacterial arts, and can be obtained from well known sources and propagated by well known methods. An exemplary source is the American Type Culture Collection (ATCC), although other culture banks are also available. The culturing of bacteria is also well known, and praticularly the preparation of spores for the sporulating varieties of bacteria, which are particularly preferred.

C. Bifidogenic Oligosaccharides

Bifidogenic oligosaccharides, as used in the context of the present invention, are a class of sugars particularly useful for preferentially promoting the growth of a lactic acid bacteria of this invention. These oligosaccharides include fructo-oligosaccharides (FOS), gluco-oligosaccharides (GOS), other long-chain oligosaccharide polymers of fructose and/or glucose, and the trisaccharide raffinose, all of which are not readily digested by pathogenic bacteria. The preferential growth is promoted due to the nutrient requirements of this class of lactic acid bacterium as compared to pathogenic bacteria. Bifidogenic oligosaccharides are polymers that are utilized almost exclusively by the indigenous *Bifidobacteria* and *Lactobacillus* and can be similarly utilized by *Bacillus*. Deleterious microorganisms such as *Clostridium, Candida, Campylobacter, Klebsiella, Pseudomonas, Staphylococcus, Salmonella* and *E. coli* cannot metabolize FOS or other bifidogenic oligosaccharides, and therefor use of these bifidogenic oligosaccharides in combination with a lactic acid bacteria of this invention, particularly *Bacillus*, allows the beneficial and probiotic bacteria to grow and to replace any undesirable or pathogenic microorganisms.

The use of bifidogenic oligosaccharides in compositions of the present invention provides a synergistic effect thereby increasing the effectiveness of the probiotic-containing compositions of this invention. This synergy is manifest at least by selectively increasing the ability of the probiotic bacterium to grow by increasing the food supplement for probiotic bacteria which preferentially selects for growth of the probiotic bacteria over many other bacterial species in the infected tissue. In addition, it is understood that *Bifidobacteria* and *Lactobacillus* are also producers of lactic acid. Bifidogenic oligosaccharides enable these probiotic organisms to proliferate preferentially over the undesirable bacteria that may be present in the tissue to be treated by the present invention, thereby furthering the probiotic state of the body. Thus, the presence of the bifidogenic oligosaccharides in the formulation allows for more effective inhibition of undesirable microbes by increasing the ability of all varieties of beneficial probiotic bacteria to grow and therefore provide benefit.

The bifidogenic oligosaccharide can be used either alone or in combination with a lactic acid bacterium in a composition. That is, due to the growth promoting activity of bifidogenic oligosaccharides, the invention also contemplates a composition comprising a bifidogenic oligosaccharide of this invention in a lactic acid bacterium growth-promoting amount. As shown herein, these amounts can vary widely since a probiotic lactic acid bacterium will respond to any metabolic amount of nutrient oligosaccharide, and therefore the invention need not be so limited.

A preferred and exemplary bifidogenic oligosaccharide is FOS, although the other sugars can also be utilized, either alone or in combination. FOS can be obtained from a variety of natural sources, including commercial suppliers. As a product isolated from natural sources, the components can vary widely and still provide the beneficial agent, namely FOS. FOS typically has a polymer chain length of from about 4 to 100 sugar units, with the longer lengths being preferred. For example, the degree of purity can vary widely so long as functional FOS is present in the formulation. Preferred FOS formulations contain at least 50% by weight of fructo-oligosaccharides compared to simple (mono or disaccharide) sugars such as glucose, fructose or sucrose, preferably at least 30% fructo-oligosaccharides, more preferably at least 90% and most preferably at least 95% fructo-oligosaccharides. Sugar content and composition can be determined by any of a variety of complex carbohydrate analytical detection methods as is well known.

Preferred sources of FOS include: inulin, Frutafit IQ™ from Imperial Suiker Unie (Sugar Land, Tex.), NutraFlora™ from Americal Ingredients, Inc., (Anaheim, Calif.), Fabrchem, Inc., (Fairfield, Conn.), and Fruittrimfat Replacers and Sweeteners (Emeryville, Calif.). Bifidogenic oligosaccharides such as GOS, and other long chain oligosaccharides are also available from commercial vendors.

D. Compositions

The present invention is directed to the discovery that lactic acid bacteria, particularly *Bacillus* species, can be used in compositions as a probiotic in combination with sanitary products for inhibiting dermal and epithelial microbial infections associated with the use of sanitary products. As discussed further, the compositions can be formulated in many configurations because the bacterium can be presented as a viable organism (e.g., as a vegetative cell or as a spore depending on the species and form of probiotic organism) and colonize tissues associated with use of a sanitary product. The cells/spores can be presented in a variety of compositions suited for use in a sanitary product.

The active ingredients (i.e., live bacteria or extracellular components, comprise about 0.1% to about 50% by weight of the final composition, preferably 1% to 10% by weight in the composition. A typical composition will contain in a one gram dosage formulation a concentration of from $10^3$ to $10^{14}$ colony forming units (CFU) of viable acid bacterium (i.e., vegetative cell) or bacterial spore, preferably $10^5$ to $10^{12}$ colony forming units/g, whereas in other preferred embodiments the concentrations are $10^9$ to $10^{13}$ colony forming units/g; $10^5$ to $10^7$ colony forming units/g; or $10^8$ to $10^9$ colony forming units/g.

In one embodiment, a composition for use in a sanitary product according to the present invention can further comprise a degradation-enhancing bacteria as described herein. A preferred amount of this bacteria is an amount sufficient to promote degradation, which can be from about $10^4$ to $10^{14}$ CFU of viable bacteria for use per unit of sanitary product, preferably about $10^7$ to $10^{10}$ CFU per unit, and more preferably about $10^8$ to $10^9$ CFU per unit. The actual amount in a composition will vary depending upon the amounts of composition to be dispersed into the absorbent structure or other portions of the sanitary product, and upon routes of dispersal.

In addition, it is contemplated that combinations of bacteria may be utilized to afford optimized formulations depending upon the circumstances. Thus, various combinations of species of bacteria may be used, and in varying amounts, so long as the primary objective is to provide a probiotic acid bacteria, and the secondary objective is to provide a degradation-enhancing bacteria.

In a preferred embodiment, the invention contemplates certain preferred combinations. In particular, a mixture of bacterial spores is ideally suited for manufacturing and shelf storage. A preferred embodiment utilizes a dispersion of about one billion CFU of *B. coagulans* spores mixed with about one billion CFU of degradation enhancing bacterial spores, preferably an equal mix of *B. licheniformis, B. subtilis, B. pumilis* and *B. megaterium*.

In one preferred embodiment a composition may further include from about 10 milligrams (mg) to one gram of a bifidogenic oligosaccharide, preferably a fructo-oligosaccharide. The composition typically contains a lactic acid bacterium growth-promoting amount of the bifidogenic oligosaccharide, which growth-promoting amount can vary widely and be readily measured by growth assays as described herein. The composition will typically contain 10 mg to 1 gm of bifidogenic oligosaccharide per gram of composition depending on the dosage, route of administration and intended usage.

The formulation for a composition of this invention may include other probiotic agents or nutrients for promoting spore germination and/or bacterial growth. A particularly preferred material is a bifidogenic factor which promotes growth of beneficial probiotic bacteria as described herein.

The compositions may also include known antimicrobial agents, known antiviral agents, known antifungal agents, all of which must be compatible with maintaining viability of the *Bacillus* active agent when *Bacillus* organisms or spores are the active agent. The other agents in the compositions can be either synergists or active agents. Preferably, the known antimicrobial, antiviral and/or antifungal agents are probiotic agents compatible with *Bacillus*. The compositions may also include known antioxidants, buffering agents, and other agents such as coloring agents, flavorings, vitamins or minerals. Thickening agents may be added to the compositions such as polyvinylpyrrolidone, polyethylene glycol or carboxymethylcellulose.

Chemicals used in the present compositions can be obtained from a variety of commercial sources, including Spectrum Quality Products, Inc (Gardena, Calif.), Seltzer Chemicals, Inc., (Carlsbad, Calif.) and Jarchem Industries, Inc., (Newark, N.J.).

The active agents are combined with a carrier that is physiologically compatible with the dermal or epithelial tissue of a human or animal to which it is administered. That is, the carrier is preferably substantially inactive except for surfactant properties used in making a suspension of the active ingredients. The compositions may include other physiologically active constituents that do not interfere with the efficacy of the active agents in the composition.

A formulated composition of this invention may be completed in weight using any of a variety of carriers and/or binders. A preferred carrier is micro-crystalline cellose (MCC) added in an amount sufficient to complete the one gram dosage total weight. Particularly preferred formulations for a composition of this invention are described in the Examples section, infra.

Carriers can be solid-based dry materials for formulations in tablet, granule or powdered form, and can be liquid or gel-based materials for formulations in liquid or gel forms, which forms depend, in part, upon the manner of use or the manner of manufacturing a sanitary product. Typical carriers for dry formulations include trehalose, malto-dextrin, rice flour, micro-crystalline cellulose (MCC) magnesium stearate, inositol, FOS, gluco-oligosaccharides (GOS), dextrose, sucrose, and the like carriers.

Where the composition is dry and includes evaporated oils that produce a tendency for the composition to cake (adherence of the component spores, salts, powders and oils), it is preferred to include dry fillers which distribute the components and prevent caking. Exemplary anti-caking agents include MCC, talc, diatomaceous earth, amorphous silica and the like, typically added in an amount of from about 1 to 95% by weight.

The carrier is preferably a formulation in which, for example, *B. coagulans* can be suspended for hydration by the user before it is administered to the sanitary product or tissue. Suitable liquid or gel-based carriers are well known in the art, such as water and physiological salt solutions, urea, alcohols and glycols such as methanol, ethanol, propanol, butanol, ethylene glycol and propylene glycol, and the like. Preferably, water-based carriers are about neutral pH.

In a related embodiment, the invention describes an aqueous liquid absorbent composition comprising an aqueous liquid absorbing medium (i.e., an "absorbent") and a microbe-inhibiting amount of an extracellular product isolated from *B. coagulans* as described herein. The absorbent composition is similar to an absorbent structure described herein for a sanitary product insofar as the composition in the absorbent portion of the sanitary product. The composition is formulated to be added to or dispersed into/onto a sanitary product for use of the product according to the methods described for a sanitary product of the present invention, that is to inhibit microbial growth upon use of the product.

The composition containing absorbent and the extracellular product is typically produced by admixing the extracellular product with a pre-selected amount of absorbent, and drying or desiccating the admixture to coat the absorbent medium with the microbe-inhibiting extracellular product. The resulting dry composition can be applied directly onto a conventional sanitary product.

The manufacture of a composition comprising the absorbent and the extracellular product involves admixing a microbe-inhibiting amount extracellular product prepared as described herein, typically in the ratio of 0.1 to 1 ml of supernatant per gram of absorbent, and thereafter drying the absorbent medium to form the microbe-inhibiting absorbent composition.

The absorbent composition may further contain a degradation-enhancing bacteria as described herein in amounts similar to the amounts used in a sanitary product on a weight and volume basis. The absorbent composition may also contain a bifidogenic oligosaccharide as described herein.

A preferred composition according to the present invention is an aqueous liquid absorbent composition that comprises an aqueous liquid absorbing medium and an effective amount of a viable lactic acid-producing bacteria according to the present invention, also referred to as an anti-microbial absorbent composition. This composition is useful for application directly onto a sanitary product and has both the absorbent and microbe inhibiting properties described herein.

The lactic acid-producing bacteria can be any of the various bacteria described herein, with lactic acid bacteria preferred, and B. coagulans being particularly preferred. The bacteria is typically provided in the composition in the form of dried cells, a dried cell mass or as spores in powder, and can also be formulated into a liquid, paste, powder, granule or pellet formulation.

An absorbent anti-microbial composition typically contains about $10^2$ to $10^{14}$ CFU viable probiotic acid bacteria per cubic meter of composition, preferably contain about $10^3$ to $10^{10}$ CFU, more preferably contain $10^3$ to $10^6$ CFU or $10^6$ to $10^9$ CFU, and in preferred embodiments contain $10^8$ to $10^9$ CFU per cubic meter of absorbent composition.

The aqueous liquid absorbing medium can be any of the materials described for an absorbent structure herein, and need not be limited. The absorbent composition can further comprise a bifidogenic oligosaccharide as described herein for an absorbent product, and typically is present in amounts of about 10 mg to 1 gm of oligosaccharide per cc of composition, and preferably about 100 to 500 mg oligosaccharide per cc of composition.

E. Methods for Inhibiting Microbial Infections

The claimed invention is directed at methods for increasing dermal and mucoidal health and inhibiting microbial infections and microbial growth associated with use of sanitary products. The method comprises the use of a sanitary product comprising a viable non-pathogenic lactic acid bacteria, which bacterial promote dermal probiosis. In a related embodiment, one can administer a composition of the present invention to a pre-existing sanitary product, and use the product. In either case, the use of the sanitary product containing bacteria provides contact between the tissue in which the probiotic effect is targeted and the sanitary product, and thereby contacts the target tissue with an effective amount of the active probiotic ingredients in the composition.

The claimed invention describes methods for inhibiting dermal or epithelial infections comprising the steps of contacting the surface of a sanitary product of this invention with the skin or mucous membrane of a mammal and maintaining the contact for a time period sufficient to allow initiation of probiotic activity of the lactic acid bacteria or spores in the sanitary product, thereby inhibiting microbial growth adjacent to or on the skin or mucous membrane contacted by the sanitary product.

Typically, the surface of the sanitary product used in the present method is present on a flexible article selected from the group consisting of a diaper, pliable material for wiping skin or a mucous membrane, dermal patch, adhesive tape, absorbent pad, clothing, tampon, panty protector, incontinence guard, sanitary napkin or the like product.

The method can be practiced to inhibit any of a variety of infections and/or irritations known to arise upon use of a sanitary product, including but not limited to diaper rash, eczema, incontinence, menstruation, fluid discharges from wounds and other dermal/epithelial infections or inflammations caused by opportunistic microbial pathogens that overgrow as a result of the irritated or inflamed skin/epithelial tissue, dermatitis, eczema, skin allergies, and the like due to use of the sanitary product.

Typically, the mammal is a human, although the methods and compositions of the invention can be applied to any mammal which would require the use of a sanitary product where dermal infections/inflammations could be problematic.

Generally, the non-pathogenic lactic acid bacteria is used according to the present invention by applying a sanitary product to a tissue, which product already contains an effective amount of the bacteria incorporated into portions of the sanitary product. Alternatively, a composition of the bacterial may be applied to the sanitary product prior to use. Administration of a composition of this invention to a sanitary product is preferably made using a gel, suspension, spray, powder or semi-solid formulation containing viable bacteria, bacterial spores and/or probiotic extracellular product, all formulated using "good manufacturing practice" (GMP) methods well known in the art. Administration comprises use of typically 0.001 (i.e., 10,000 CFU) to 10 billion colony forming units (CFU) of viable bacteria or spore applied to a unit of sanitary product, although lesser or greater amounts may also be used. Application is preferably by way of spray-drying a spore/bacteria/extracellular product liquid suspension onto the sanitary product's absorbent structure, preferably onto the region of the sanitary product which directly contacts the dermal/epithelial tissue upon use.

Upon use of the sanitary product, the absorbent structure acquires a body fluid, such as urine, excess fluid of fecal matter, blood, tissue exudate, pus, and the like depending upon the type of sanitary product, whereupon the fluid comes into contact with the lactic acid bacteria present in the sanitary product. The bacteria germinates or is motivated to grow as a result of the contact with the body fluid, and using the electrolytes and substrates present in the body fluid proliferates. Upon growth, the bacterial produces metabolites that are effective in mitigating mycotic growth and other microbial pathogens. In addition, the growth of the bacterial feeds on the body fluid waste, and produces enzymes with facilitate degradation of the sanitary product. After the sanitary product is removed and disposed into a landfill, the bacterial continue to grow and degrade the waste and materials present in the construction of the sanitary product.

In preferred embodiments where a bifidogenic oligosaccharide is included in a composition of this invention, such as FOS, there is a synergy provided in the form of a selective food supply, as described herein, resulting in selective growth of acid bacteria over food supply-driven growth of pathogenic bacterial.

The method comprises administration of a composition of this invention containing the active ingredients to a human or animal in various dosage regimens as described herein to achieve the nutritional result. The method is typically practiced on any animal where inhibiting microbial infection is desired. Typically, a human in the preferred user of a sanitary product or composition according to the present invention, although the invention can be practiced on any mammal. The mammal can be any livestock or zoological specimen where such inhibition of parasites/pathogens provides economic and health benefits. Any animal can benefit by the claimed methods, including horses, cows, sheep, goats, pigs, and the like domesticated animals. Other purposes are readily apparent to one skilled in the arts of sanitary products.

In carrying out the methods of the invention, it is appreciated that there are multiple benefits and advantages. In particular, it is noted that the presence of the lactic acid-producing bacteria will promote degradation of used sanitary products, when used either alone or in combination with other bacteria. In addition, as shown herein, viable lactic acid bacterial growth will exhibit a beneficial probiotic effect onto the skin or epithelial tissue adjacent to the sanitary product in use by out-competing dermal/epithelial pathogens, and by production of extracellular metabolites that inhibit dermal/epithelial pathogens.

In a related embodiment, the invention contemplates a method for enhancing biodegradation of a sanitary product comprising the step of providing an inoculum of viable non-pathogenic lactic acid-producing bacteria according to this invention into the sanitary product, and contacting the sanitary product to the body tissue for use as prescribed/intended for the sanitary product. The presence of the provided inoculum in the used sanitary product together with the collected body fluids/exudates provides an environment for bacterial growth, which facilitates the breakdown of the various components of the sanitary product, including the waste material containing in the disposed sanitary product and the various components making up the sanitary product, such as cellulose, petroleum hydrocarbon polymers, natural and synthetic fibers and adhesives, and the like materials described herein for constructing a sanitary product.

As noted above, enhancement of degradation of a sanitary product upon disposal can be facilitated by use of a lactic acid bacteria. In a particular embodiment, the method comprises the use of a non-pathogenic lactic acid bacteria and comprises the use of one or more additional species of bacteria designed to enhance degradation. These additional bacteria are non-pathogenic insofar as they are included in the sanitary product, but are not necessarily probiotic in terms of inhibiting dermal or epithelial microbial infections. Rather, these additional bacteria are included solely for the ability to enhance degradation, and are referred collectively as "degradation-enhancing" bacteria.

F. Articles of Manufacture

The invention also contemplates various articles of manufacture which utilize the beneficial aspects of the present invention by combination of a composition with various medical or personal hygiene devices so as to reduce or prevent microbial infections associated with the use of these devices. The invention comprises compositions of a probiotic lactic acid bacteria, preferably a lactic acid bacteria, and more preferably a *Bacillus* species and/or isolated *B. coagulans* active agent, applied to a solid surface or impregnated into a solid matrix of any device or article of manufacture that is intended to be in contact with skin or a mucous membrane. Preferably the solid surface is a flexible article than can be worn on or wiped on the skin or mucous membrane. More preferably, when the flexible item carrying the acid bacteria is to be worn on the skin it includes a means for attaching the article to the skin such as, for example, an adhesive layer, interengaging hook and pile (i.e., Velcro®) connectors, or other well known means of attachment such as ties, snap closures, elastic, buttons, and the like.

Many different types of absorbent products having absorbent structures are well known in the art, and can include diapers, towelettes (e.g., baby wipes or feminine hygiene towelettes), sanitary napkins, tampons, panty protectors, dermal patches, adhesive tape, bandages, wound or sore dressings, absorbent pads, incontinence guards, bed sheets or protectors, saliva absorbent, articles of clothing (e.g., underclothes, sleeping apparel), bath towels, wash cloths, and the like. Thus, the claimed invention describes an absorbent product comprising an aqueous liquid absorbent structure and an effective amount of viable non-pathogenic acid bacteria according to said invention.

Absorbent structures in sanitary products (absorbent products) are typically produced by fluffing cellulosic or other fibrous pulp into a roll, bale or sheet for instance, to form a pulp mat, sometimes admixed with so-called superabsorbent materials in the pulp mat. The superabsorbent materials are typically polymeric formulations capable of absorbing many times their own weight of water of body fluid, and are well known in the art. The pulp mat is typically compressed so as to enhance its fluid-wicking ability and also in order to reduce pulp body bulk, and therewith obtain an article which is as compact as possible to achieve the absorbent properties desired in the particular sanitary product.

The absorbent structure may also include other constituents, for example, components which will improve fluid acquisition properties, fluid-wicking properties, fluid retention properties, and the like well known in the art. Other included constituents include components which increase coherent strength (i.e., the ability to withstand deformation during use). The absorbent structure may contain fibrous woven, knitted or non woven materials, occlusive or non-occlusive films or membranes, granules, pellets or aggregates of absorbent material, synthetic polymer fibers, films, membranes and foams (e.g., nylon, polytetrafluoroethylene (PTFE, such as Teflon® or Gor-Tex®), polystyrene, polycarbonate, polyvinylchloride and polysulphone). All of these forms are well known in the art and include, for example, knitted or woven fabrics, non-woven fabrics such as felt and batting, fiber balls of cotton, rayon, cellulose or synthetic fibers, and the like materials.

The fibers can be natural fibers, including but not limited to: wool, silk, cotton, cellulosic fiber, and the like natural fibers. Natural polymers based on polysaccharide can also be used, including, but not limited to: modified cellulose and cellulose derivatives (e.g., alkyl-, hydroxyalkyl-, carboxymethylcellulose); gum resins (e.g., guar gum, locust bean gum, tragacanth gum, gum arabic, pectin, etc.); starch and starch derivatives (e.g., corn starch, grain starch, potato starch, amylose, amylopectin, dextrin, dextran, modified starch, hydroxy-ethyl starch, cationic starch, starch graft polymers, and the like polymers). The fibers can be synthetic fibers, including, but not limited to: polyester, polyolefin, polyamide, polyvinyl alcohol, polyvinyl acetate, polyvinyl chloride, polyvinyl urea, polyurethane, polyurea, polyacrylonitrile, as well as copolymers of these polymers, and the like synthetic fibers.

The absorbent product can be formatted into a multi layer configuration, having an absorbent structure layer, a fluid permeable top layer which allows wicking of fluid but is itself non-wettable due to its structural composition (e.g., synthetic fiber construction), and a fluid-impermeable bottom layer (i.e., back sheet) which prevents absorbed fluid to pass from the absorbent structure layer to the adjacent tissues of the user when contacted by the absorbent product during use. Such layered configurations are well known in the diaper and panty liner arts, and need not be described in detail.

The absorbent product typically contains about $10^2$ to $10^{14}$ CFU of viable probiotic acid bacteria per cubic meter ($M^3$) of absorbent product, and is typically dispersed in the form of cells, dried cell mass or spores, with spores being the particularly preferred format. Preferably, the product will contain about $10^3$ to $10^{10}$ CFU per $M^3$ of absorbent product, and may have $10^3$ to $10^6$ CFU per $M^3$ or $10^6$ to $10^9$ CFU per $M^3$, and preferably will have $10^8$ to $10^9$ CFU per $M^2$ of absorbent product, although these amounts can vary depending upon the specific application, product formulation and intended use.

The absorbent product may further contain a bifidogenic oligosaccharide dispersed therein as described for a composition according to the present invention, typically in amounts of from about 10 milligrams (mg) to 1 gram per cubic centimeter (cc) of absorbent structure, and preferably about 100 to 500 mg of oligosaccharide per cc of structure.

The absorbent product may further contain a degradation-enhancing bacteria according to the present invention, as described herein. Where the degradation-enhancing bacteria is different from the probiotic lactic acid-producing bacteria, the degradation enhancing bacteria can be incorporated into the absorbent product is regions of the product designed to keep the bacteria away from the skin or tissues of the mammal during use, and designed for release or access to the waste products. Typically, an absorbent product will contain from $10^4$ to $10^{14}$ CFU of viable degradation-enhancing bacteria per unit of sanitary product, preferably about from $10^7$ to $10^{10}$ CFU per unit, and more preferably about from $10^8$ to $10^9$ CFU per unit.

A composition containing a lactic acid bacteria of this invention can be applied to any of a variety of regions of an absorbent product of the present invention including the moisture barrier (i.e., the "stay-dry lining"), the absorbent structure (e.g., moisture absorbing polymer), coated onto the external surface that contacts the skin or epithelial tissue, in capsules which are sealed-off until wetted for slow release of bacteria/spores, or combinations thereof. The bacteria can be presented as a spore, a dry or lyophilized cell mass, a stabilized gel or paste, a dry powder, or as a component of the gel polymer that comprises the moisture barrier system.

In addition, insofar as the *Bacillus coagulans* extracellular product (i.e., the "isolated agent") can be used to inhibit microbial pathogens, the invention contemplates the use of the extracellular product in place of or in combination with a viable acid bacteria in any of the sanitary products described herein.

The lactic acid bacteria and/or a *B. coagulans*-isolated active agent can be applied to the solid surface using any of a variety of known methods including, for example, applying a powder, spray drying the probiotic onto the material or soaking the material in a solution containing the probiotic and then using the wetted material or drying the material before use. Porous material may contain the *Bacillus* and/or the isolated active agent in the pores or interstices of the solid material. The *Bacillus* and/or the isolated active agent can be attached by adhesion, such as by attachment to an adhesive layer that is then applied to the skin (e.g., in a bandage or dermal patch). The *Bacillus* and/or the isolated active agent can be impregnated into the solid material during the manufacturing process of the flexible article (e.g., added to a synthetic composition before or during the polymerization process). The pressure and heat resistance of *Bacillus* spores makes them particularly suitable for incorporation into the material during manufacturing.

Any of the solid materials carrying *Bacillus* and/or the isolated active agent can be packaged individually or in groups, suitable for holding the treated material using standard packaging materials (e.g., in a shrink wrapper, sealed packet, protective wrapper or dispensing container suitable for holding dry or wet materials) The article of manufacture can have applied thereon any of the additional/optional components of a composition of this invention, including carriers, disinfectants, antibacterial agents, salts, FOS, and the like. In particular, the absorbent product can include as a component part of the absorbent structure inert ingredients, neutral filling agents, and the like. Exemplary neutral filling agents include peat, sand, clay, garden mold, ground shells of nuts or pomaceous fruit, wood flour, chitin-containing flour, and the like well known materials.

Any of a variety of methods for placing the composition onto a subject article can be used, and therefor the invention need not be so limited. However, preferred methods include a "spray-dry" method in which the material is exposed in a low humidity chamber to an atomized mix containing a liquid composition, where the chamber is subsequently exposed to about 80-110° F. to dry the liquid, thereby impregnating the material of the article with the components of the composition. A typical load is from $10^5$ to $10^9$ CFU of bacteria/spores per ml of atomizing mix, to place that same amount on about one square inch of external surface of fibrous carrier/article material. The dry article is then ready for storage in a sterile package for use.

In one embodiment, the invention contemplates the use of viable probiotic acid bacteria in absorbent structures which structures are incorporated into an absorbent product as described herein. Thus, the invention describes the use of an effective amount of probiotic lactic acid bacteria where the bacteria is dispersed or incorporated in the form of dried cells or cell mass or as spores into the absorbent structure of an absorbent product according to the invention.

G. Therapeutic Systems for Inhibiting Infections Associate with Use of Sanitary Products The claimed invention further contemplates a system for inhibiting dermal or epithelial infection associated with use of a sanitary product comprising a container comprising label and an absorbent composition according to the present invention, wherein said label comprises instructions for application of the absorbent composition for inhibiting microbial infections during use of the sanitary product.

Typically, the system is present in the form of a package containing a composition or absorbent product of this invention, or in combination with packaging material. The packaging material includes a label or instructions for use of the components of the package. The instructions indicate the contemplated use of the package component as described herein for the methods or compositions of the invention.

For example, a system can comprise one or more unit dosages of a composition according to the invention. Alternatively, the system can contain bulk quantities of a composition. The label contains instructions for using the composition or absorbent product as appropriate, and may include information regarding storage of the composition or absorbent product, application methods, health indications, methods for disposal, and the like information.

Unless defined otherwise, all scientific and technical terms used herein have the same meaning as commonly understood by those skilled in the relevant art. Unless mentioned otherwise, the techniques employed or contemplated herein are standard methodologies well known to one of ordinary skill in the art. The Examples of embodiments are for illustration only.

EXAMPLES

The following Examples relating to this invention are illustrative and should not, of course, be construed as specifically limiting the invention. Moreover, such variations of the invention, now known or later developed, which would be within the purview of one skilled in the art are to be considered to fall within the scope of the present invention hereinafter claimed.

Example 1

Preparation of Bacillus coagulans Cultures

Bacillus coagulans Hammer bacteria (ATCC Accession No. 31284) was inoculated and grown to a cell density of about $10^8$ to $10^9$ cells/ml in nutrient broth containing 5 g Peptone, 3 g Meat extract, 10-30 mg $MnSO_4$, and 1,000 ml distilled water, adjusted to pH 7.0, using a standard airlift fermentation vessel at 30° C. The range of $MnSO_4$ acceptable for sporulation is 1 mg/l to 1 g/l. The vegetative cells can actively reproduce up to 45° C., and the spores are stable up to 90° C. After fermentation, the B. coagulans bacterial cells or spores are collected using standard methods (e.g., filtration, centrifugation) and the collected cells and spores can be lyophilized, spray dried, air dried or frozen. As described herein, the supernatant from the cell culture can be collected and used as an extracellular agent secreted by B. coagulans which has antimicrobial activity useful in a formulation of this invention.

A typical yield from the above culture is in the range of about $10^9$ to $10^{10}$ viable spores and more typically about 100 to 150 billion cells/spores per gram before drying. Spores maintain at least 90% viability after drying when stored at room temperature for up to ten years, and thus the effective shelf life of a composition containing B. coagulans Hammer spores at room temperature is about 10 years.

Example 2

Preparation of Bacillus coagulans Spores

A culture of dried B. coagulans spores was alternately prepared as follows. Ten million spores were inoculated into a one liter culture containing 24 g potato dextrose broth, 10 g of enzymic-digest of poultry and fish tissue, 5 g of FOS and 10 g MnSO4. The culture was maintained for 72 hours under a high oxygen environment at 37° C. to produce culture having about 150 billion cells per gram of culture. Thereafter, the culture was filtered to remove culture medium liquid, and the bacterial pellet was resuspended in water and freeze-dried. The freeze-dried powder is then ground to a fine powder using standard good manufacturing practice (GMP).

Example 3

Preparation of Bacillus coagulans Extracellular Products

A one liter culture of B. coagulans was prepared as described in Example 1. The culture was maintained for 5 days as described, at which time FOS was added at 5 g/liter, and the culture was continued. 20 ml of carrot pulp was then added at day 7, and the culture was harvested when the culture became saturated (i.e., no substantial cell division). The culture was first autoclaved for 30 minutes at 250° F., and then centrifuged at 4000 rpm for 15 mm. The resulting supernatant was collected and filtered in a Buchner funnel through a 0.8 micron (μm) filter, and the filtrate (i.e., the "pass-through") was collected and further filtered through a 0.2 μm Nalge vacuum filter. The resulting pass-through was collected (about 900 ml) to form a liquid containing an extracellular product, and used in inhibition studies.

Following the assay described in Example 5, except using Candida albicans, 1 ml of the above-produced extracellular product was added to the test plate in place of live B. coagulans. After the same culturing time, a zone of inhibition of about 10 to 25 millimeters was observed, indicating a potent antimicrobial activity of "excellent" quality, using the terminology set forth in Example 5.

Example 4

Formulations

| Formulation 1: (Powder for Application to Sanitary Product) | |
|---|---|
| B. coagulans | 250,000,000 spores (approximately 17.5 mg) |
| Fructo-oligosaccharides (FOS) | 100 mg |
| Micro-crystalline cellulose (MCC) | 372.5 mg |
| Formulation 2: (Diaper-Sanitary Product) Lined diaper containing a composition of: | |
| B. coagulans | 1 billion spores (approximately 70 mg) |
| Fructo-oligosaccharides (FOS) | 500 mg |
| Micro-crystalline cellulose (MCC) dispersed uniformly in the absorbent fibers of the diaper. | 1 g |
| Formulation 3: (Diaper - Sanitary Product) Lined diaper containing a composition of: | |
| B. coagulans | 1 billion spores (approximately 70 mg) |
| B. licheniformis | 250 million spores |
| B. subtilis | 250 million spores |
| B. pumilis | 250 million spores |
| B. megaterium | 250 million spores |
| Fructo-oligosaccharides (FOS) | 500 mg |
| Micro-crystalline cellulose (MCC) dispersed uniformly in the absorbent fibers of the diaper. | 1 g |

Example 5

Antimicrobial Activity of Bacillus coagulans

The ability of B. coagulans to inhibit bacterial pathogens was demonstrated using an in vitro assay. The assay is part of a standard bacterial pathogen screen (U.S. Food and Drug Administration) and is commercially available on solid support disks (DIFCO® BACTROL® disk set). In the assay, potato-dextrose plates (DIFCO®) were prepared using standard procedures and were inoculated individually with a confluent bed $1.5 \times 10^6$ of each species of bacteria tested. Inhibition by B. coagulans was tested by placing on the plate about $1.5 \times 10^6$ CFU in 10 μl of broth or buffer, plated directly in the center of the potato-dextrose plate with one test locus of about 8 mm in diameter per plate. A minimum of three test loci were used for each assay. The negative control was comprised of a 10 μl drop of a sterile saline solution, whereas the positive control was comprised of a 10 μl volume of glutaraldehyde. The plates were then incubated for about 18 hr at 30° C. when the zone of inhibition was measured.

As used herein, "excellent inhibition" means the zone was 10 mm or greater in diameter; and "good inhibition" means the zone was greater than 2 mm in diameter, but less than 10 mm in diameter.

No inhibition was seen with the negative control and excellent inhibition (about 16.2 mm diameter, average of three tests) was seen with the positive control. For the enteric organisms tested, *Clostridium* species and *E. coli*, excellent inhibition by *B. coagulans* was seen. For the *Clostridium* species, *C. perfringens*, *C. difficile*, *C. botulinum*, *C. tributrycum* and *C. sporogenes*, the zone of inhibition was consistently greater than 15 mm in diameter. Similarly, excellent inhibition was also seen for the opportunistic pathogens *Pseudomonas aeruginosa*, *Staphylococcus aureus*, and *Candida species*.

The present invention has been described in the above Examples using a variety of formulations, although it should be apparent that various other carrier agents that are compatible with the probiotic compositions may be substituted in the examples to give similar results. Accordingly, the present invention may be embodied in other specific forms without departing from it in spirit. The Examples are to be considered in all respects only as illustrative and not as restrictive, and the scope of the invention is indicated by the claims that follow. All modifications which come within the meaning and range of the lawful equivalency of the claims are to be embraced within their scope.

What is claimed is:

1. A method of inhibiting or preventing a skin infection in a subject suffering from said skin infection or at risk thereof, comprising the step of applying to the skin of the subject an absorbent product comprising a fabric and viable non-pathogenic *Bacillus coagulans* bacteria, wherein said fabric is woven or non-woven, and wherein said bacteria are present on an external surface of said absorbent product, thereby inhibiting or preventing said skin infection.

2. The method of claim 1, wherein said absorbent product is a diaper, towelette, sanitary napkin, tampon, panty protector, incontinence guard, bed sheet, bed protector, clothing, wound or sore dressing, dermal patch, adhesive tape, saliva absorbent product, wash cloth, or bath towel.

3. The method of claim 1, wherein said bacteria are present in the form of spores.

4. The method of claim 1, wherein said bacteria are present in the form of a dried cell mass.

5. The method of claim 1, wherein said bacteria are incorporated into the absorbent product in a liquid, paste, powder, granule, or pellet formulation.

6. The method of claim 1, wherein said absorbent product contains $10^2$ to $10^{14}$ of viable bacteria or spores per cubic meter of absorbent product.

7. The method of claim 1, wherein said absorbent product contains $10^6$ to $10^9$ of viable bacteria or spores per cubic meter of absorbent product.

8. The method of claim 1, wherein said *Bacillus coagulans* is *Bacillus coagulans* Hammer.

9. The method of claim 1, wherein said absorbent product further comprises a degradation-enhancing, non-pathogenic bacteria that is not *Bacillus coagulans* selected from the group consisting of a member of the *Bacillus* genus, the *Lactobacillus* genus, the *Sporolactobacillus* genus, the *Bifidobacterium* genus, and the *Pseudomonas* genus.

10. The method of claim 1, wherein said absorbent product further comprises an extracellular product of *Bacillus coagulans* bacteria.

11. The method of claim 1, wherein said absorbent product is disposable.

12. The method of claim 1, wherein said absorbent product comprises a liquid non-permeable back sheet adjacent to an absorbent matrix.

13. The method of claim 1, wherein said absorbent product comprises fibers, non-woven fabric, pellets or aggregates of absorbent material.

14. The method of claim 1, wherein said absorbent product comprises fibers selected from the group consisting of cellulose, cotton, silk, wool, polyester, polyolefin, polyamide, polyvinyl alcohol, polyurethane, polyurea, and polyacrylonitrile.

15. The method of claim 1, wherein said absorbent product comprises a porous material comprising non-woven fabric.

16. The method of claim 1, wherein said absorbent product further comprises an antimicrobial agent, an antiviral agent, or an antifungal agent.

17. The method of claim 1, wherein said absorbent product further comprises a fructooligosaccharide (FOS).

18. The method of claim 1, wherein said skin infection is caused by a *Staphylococcus* species or a *Streptococcus* species.

19. The method of claim 1, wherein said skin infection is a dermal or epithelial infection.

20. The method of claim 1, wherein said fabric comprises felt and batting, fiber balls of cotton, rayon, cellulose or synthetic fibers.

21. The method of claim 1, wherein said absorbent product further comprises foam.

22. A method of inhibiting or preventing a skin infection in a subject suffering from said skin infection or at risk thereof, comprising the step of applying to the skin of the subject an absorbent product comprising a fabric and an extracellular supernatant of non-pathogenic *Bacillus coagulans* bacterial cells, said supernatant in liquid or powder form, wherein said fabric is woven or non-woven, and wherein said supernatant is present on an external surface of said absorbent product, thereby inhibiting or preventing said skin infection.

* * * * *